United States Patent [19]

Ziman

[11] 4,362,548
[45] Dec. 7, 1982

[54] HERBICIDAL AND PLANT-GROWTH-REGULATING N-SUBSTITUTED-N-(2,5-DIALKYLPYRROL-1-YL) HALOACETAMIDES

[75] Inventor: Stephen D. Ziman, San Francisco, Calif.

[73] Assignee: Chevron Research Company, San Francisco, Calif.

[21] Appl. No.: 229,371

[22] Filed: Jan. 29, 1981

Related U.S. Application Data

[62] Division of Ser. No. 60,320, Jul. 25, 1979, Pat. No. 4,282,028.

[51] Int. Cl.³ .................... A01N 43/80; C07D 275/02
[52] U.S. Cl. ........................................ 71/90; 548/214
[58] Field of Search ........................... 548/214; 71/90

[56] References Cited

U.S. PATENT DOCUMENTS

| | | | |
|---|---|---|---|
| 3,907,544 | 9/1975 | Olin | 71/95 |
| 3,944,607 | 3/1976 | Chan | 260/558 |
| 4,021,224 | 5/1977 | Pallos et al. | 71/90 |
| 4,055,410 | 10/1977 | Cheng | 71/90 |
| 4,097,262 | 7/1978 | Cheng | 71/90 |
| 4,104,051 | 8/1978 | Cheng | 71/92 |
| 4,141,989 | 2/1979 | Chan | 424/279 |
| 4,155,745 | 5/1979 | Walker | 71/88 |
| 4,221,584 | 9/1980 | Ziman | 548/214 |
| 4,224,050 | 9/1980 | Calle et al. | 71/98 |

FOREIGN PATENT DOCUMENTS

| | | |
|---|---|---|
| 863565 | 2/1978 | Belgium . |
| 2702102 | 7/1978 | Fed. Rep. of Germany . |
| 2805525 | 8/1978 | Fed. Rep. of Germany . |
| 1585243 | 2/1981 | United Kingdom . |

*Primary Examiner*—Donald G. Daus
*Assistant Examiner*—M. C. Eakin
*Attorney, Agent, or Firm*—D. A. Newell; T. G. De Jonghe; L. S. Squires

[57] ABSTRACT

Compounds of the formula:

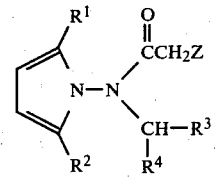

wherein $R^1$ and $R^2$ are alkyl or halo; $R^3$ is hydrogen or alkyl; Z is halo; and $R^4$ is alkoxycarbonyl, alkoxy, phenyl, substituted phenyl, a group of the formula

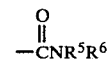

wherein $R^5$ and $R^6$ are hydrogen, alkyl, alkenyl or alkynyl; a group of the formula

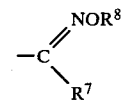

wherein $R^7$ and $R^8$ are hydrogen or alkyl; A five or six-membered aromatic heterocyclic ring of the formula

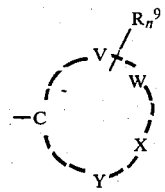

wherein at least one of V, W, X or Y is an oxygen, sulfur or nitrogen atom, $R^9$ is alkyl and n is 0, 1, 2 or 3 have herbicidal and plant-growth-regulating activity.

5 Claims, No Drawings

HERBICIDAL AND PLANT-GROWTH-REGULATING N-SUBSTITUTED-N-(2,5-DIALKYLPYRROL-1-YL) HALOACETAMIDES

This application is a division of Ser. No. 60,320, 7-25-79, now U.S. Pat. No. 4,282,028.

BACKGROUND OF THE INVENTION

Many N-substituted-N-phenyl-haloacetamides are known. For example, compounds containing heterocyclic N-substituents are disclosed in U.S. Pat. Nos. 3,907,544, 4,055,410, 4,097,262, 4,104,051, Offenlegungsschrift Nos. 2,702,102, 2,805,525, and in Belgian Pat. No. 863,565.

Other N-phenyl-haloacetamides having amido-containing substituents are disclosed in U.S. Pat. Nos. 3,944,607 and 3,097,544. Examples of alkoxycarbonyl and alkoxy-containing N-substituents are disclosed in Offenlegungsschrift No. 2,805,525.

In U.S. Pat. No. 4,141,989, commonly assigned herewith, there are disclosed fungicidal N-butyrolactone-N-dimethylphenyl-chloroacetamides.

SUMMARY OF THE INVENTION

I have invented a novel class of N-substituted-N-(2,5-dialkylpyrrol-1-yl) haloacetamides which exhibit herbicidal and plant-growth-regulating activity, herbicidal and plant-growth-regulating compositions thereof and methods of their use. Although a large class of N-substituted-N-(dialkylphenyl) haloacetamides is known, none wherein the dialkylphenyl group has been replaced by a dialkylpyrrol group, as according to my invention, is known. The compounds of the invention are generally effective in both pre- and post-emergent applications and are particularly selective in pre-emergent applications against grassy weeds.

DESCRIPTION OF THE INVENTION

The compounds of the invention are represented by the formula (I):

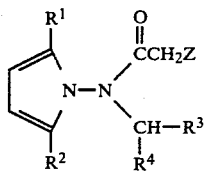

wherein $R^1$ and $R^2$ are alkyl of 1 to 3 carbon atoms or halo; $R^3$ is hydrogen or alkyl of 1 to 3 carbon atoms; Z is halo; and $R^4$ is alkoxycarbonyl of 2 to 6 carbon atoms alkoxy of 1 to 4 carbon atoms; phenyl optionally substituted with 1 to 4 of the same or different substituents selected from halo, alkyl of 1 to 4 carbon atoms or alkoxy of 1 to 4 carbon atoms;

a group of the formula

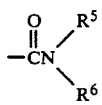

wherein $R^5$ and $R^6$ are individually hydrogen, alkyl of 1 to 4 carbon atoms, alkenyl of 2 to 4 carbon atoms, or alkynyl of 2 to 4 carbon atoms;

a group of the formula

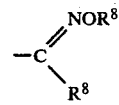

wherein $R^7$ and $R^8$ are individually hydrogen of alkyl of 1 to 4 carbon atoms;

a five or six-membered aromatic heterocyclic ring of the formula

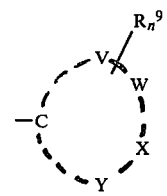

wherein at least one of V, W, X and Y is an O, S or N atom and V, W, X and Y are individually C, O, N or S; $R^9$ is alkyl of 1 to 4 carbon atoms or phenyl, and n is 0, 1, 2 or 3.

Representative $R^1$ and $R^2$ groups are chloro, bromo, fluoro, methyl, ethyl, i-propyl, n-propyl. Preferably $R^1$ and $R^2$ are methyl.

Representative Z groups are chloro, fluoro, bromo, iodo. Preferably Z is chloro.

Representative $R^3$ alkyl groups are methyl, ethyl, n-propyl, i-propyl. Preferably $R^3$ is hydrogen or methyl.

Representative $R^4$ groups are methoxycarbonyl, ethoxycarbonyl, methoxy, ethoxy, propoxy, N,N-dimethylcarbamido, N-methyl-N-ethyl-carbamido, N-methyl-N-allyl-carbamido and N-methyl-N-propargyl-carbamido, phenyl, p-chlorophenyl, p-methoxyphenyl,2,6-di-methylphenyl.

When $R^4$ is an oxime, representative $R^7$ and $R^8$ groups are hydrogen, methyl, ethyl, n-propyl, i-propyl. Preferably $R^7$ and $R^8$ are methyl.

Preferably $R^4$ is a five-membered aromatic heterocyclic ring containing from 1 to 3 hetero atoms. Representative rings are 1,2,4-oxadiazol-5-yl, 3-methyl-1,2,4-oxadiazol-5-yl, furan-2-yl, 3-methyl-1,2-oxazol-5-yl, 1,2-oxazol-3-yl, 2-methyl-1,3-thiazol-5-yl, 1,2-thiazol-3-yl, 4-methyl-1,3-thiazol-5-yl. Preferably the ring contains two hetero atoms. Most preferably $R^4$ is a thiazole ring optionally substituted with an alkyl group of 1 to 4 carbon atoms preferably a methyl group.

The compounds of the invention may generally be made as follows:

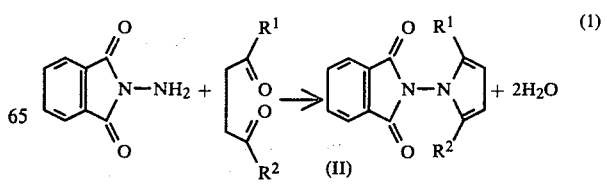

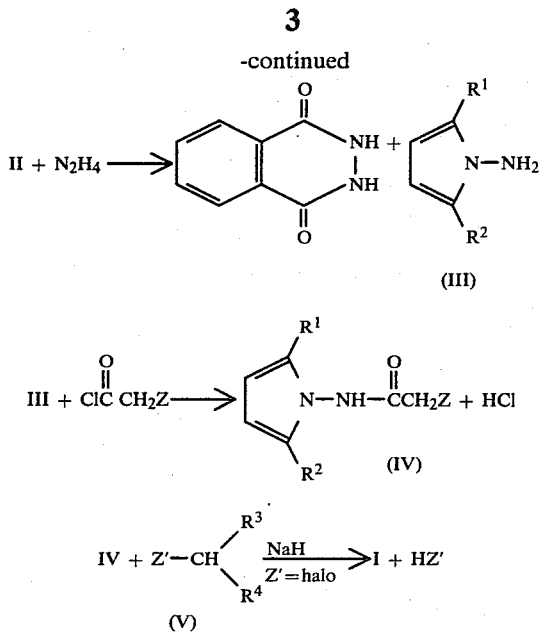

Reactions (1) and (2) are known reactions (*Chem. and Industry*, 1965, p. 425). Reaction (3) is a conventional acylation and may be accomplished by reacting substantially equimolar amounts of the amino-pyrrole and haloacetyl chloride at room temperature in an inert solvent. An equimolar amount of an organic amine, such a pyridine or a trialkylamine, may be added to scavenge the hydrogen chloride by-product.

Reaction (4) may be conducted by combining substantially equimolar amounts of the N-haloacetyl pyrrole (IV), compound (V) and sodium hydride in an inert solvent at from about −15° C. to about 30° C. If the desired product (I) is to be an oxime, then the reactant (V) may contain the corresponding carbonyl moiety in the $R^4$ substituent. The product of reaction (4) may then be reacted with hydroxylamine or alkoxylamine to produce the desired oxime.

The compounds of the present invention are, in general, herbicidal in both pre- and post-emergent applications. For pre-emergent control of undesirable vegetation, the herbicidal compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are effective against weed grasses as well as broad-leaved weeds. Some may be selective with respect to the type of application and/or type of weed. The compounds are particularly effective as pre-emergent herbicides against grassy weeds.

The compounds, when applied to growing plants above the ground in such an amount that the compounds will not kill beneficial plants, also show efficient plant growth regulating or retarding effects and may be advantageously employed, for example, to prevent or retard the growth of lateral buds in plants and to promote the thinning out of superfluous fruits in various fruit trees.

The compounds can be applied in any of a variety of compositions. In general, the compounds can be extended with a carrier material of the kind used and commonly referred to in the art such as inert solids, water and organic liquids.

The compounds will be included in such compositions in sufficient amount so that they can exert an herbicidal or growth-regulating effect. Usually from about 0.5 to 95% by weight of the compounds are included in such formulations.

Solid compositions can be made with inert powders. The compositions thus can be homogeneous powders that can be used as such, diluted with inert solids to form dusts, or suspended in a suitable liquid medium for spray application. The powders usually comprise the active ingredient admixed with minor amounts of conditioning agent. Natural clays, either absorptive, such as attapulgite, or relatively non-absorptive, such as china clays, diatomaceous earth, synthetic fine silica, calcium silicate and other inert solid carriers of the kind conventionally employed in powdered herbicidal compositions can be used. The active ingredient usually makes up from 0.5–90% of these powder compositions. The solids ordinarily should be very finely divided. For conversion of the powders to dusts, talc, pyrophyllite, and the like, are customarily used.

Liquid compositions including the active compounds described above can be prepared by admixing the compound with a suitable liquid diluent medium. Typical of the liquid media commonly employed are methanol, benzene, toluene, and the like. The active ingredient usually makes up from about 0.5 to 50% of these liquid compositions. Some of these compositions are designated to be used as such, and others to be extended with large quantities of water.

Compositions in the form of wettable powders or liquids can also include one or more surface-active agents, such as wetting, dispersing or emulsifying agents. The surface-active agents cause the compositions of wettable powders or liquids to disperse or emulsify easily in water to give aqueous sprays.

The surface-active agents employed can be of the anionic, cationic or nonionic type. They include, for example, sodium long-chain carboxylates, alkyl aryl sulfonates, sodium lauryl sulfate, polyethylene oxides, lignin sulfonates and other surface-active agents.

When used as a pre-emergent treatment, it is desirable to include a fertilizer, an insecticide, a fungicide or another herbicide.

The amount of compound or composition administered will vary with the particular plant part or plant growth medium which is to be contacted, the general location of application—i.e., sheltered areas such as greenhouse, as compared to exposed areas such as fields—as well as the desired type of control. Generally for both pre- and post-emergent herbicidal control, the compounds of the invention are applied at rates of 0.2 to 60 kg/ha, and the preferred rate is in the range 0.5 to 40 kg/ha. For plant growth regulating or retarding activity, it is essential to apply the compounds at a concentration not so high as to kill the plants. Therefore, the application rates for plant growth regulating or retarding activity will generally be lower than the rates used for killing the plants. Generally, such rates vary from 0.1 to 5 kg/ha, and preferably from 0.1 to 3 kg/ha.

Herbicidal and plant-growth-regulating tests on representative compounds of the invention were made using the following methods.

Pre-Emergent Herbicidal Test

An acetone solution of the test compound was prepared by mixing 375 mg of the compound, 118 mg of a nonionic surfactant and 18 ml of acetone. 10 ml of this solution was added to 40 ml of water to give the test solution.

Seeds of the test vegetation were planted in a pot of soil and the test solution was sprayed uniformly onto the soil surface at a dose of 27.5 micrograms/cm$^2$. The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests appear in Table A.

Post-Emergent Herbicidal Test

The test compound was formulated in the same manner as described above for the pre-emergent test. This formulation was uniformly sprayed on 2 similar pots of 24-day-old plants (approximately 15 to 25 plants per pot) at a dose of 27.5 microgram/cm$^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear in Table A.

Root Inhibition of Watergrass Seedlings

Ten watergrass seeds were placed in each of several Northrup-King Seed-Pack growth pouches. To each pouch was added 15 ml of a 40 ppm aqueous solution of the test compound. The pouches were suspended in containers under 125–150 foot-candles of light for six days at room temperature. Root length is measured for each species and expressed as percent inhibition compound to check samples treated with the standard MH-30.

Compounds 8, 9, 10, 11 and 12 exhibited root inhibition of 47%, 47%, 30%, 38% and 52%, respectively.

For comparison to compounds of the invention, the compounds in Table II were prepared. Compound A is the product of Example 2. It can be seen in Table A that Compound A has no measurable herbicidal activity. Compound B is similar to 3-(N-chloroacetyl-N-2,6-dimethylphenylamino)-gamma-butyrolactone (U.S. Pat. No. 4,141,989) except that a 2,5-dimethyl-pyrrol-1-yl group has been substituted in place of the 2,6-dimethylphenyl group. Compound B has virtually no herbicidal activity, whereas the compounds are unexpectedly herbicidally active as shown in Table A.

Example 1—Preparation of 2,5-dimethyl-1-amino pyrrole

A mixture of N-amino-phthalimide (50 g) and 2,5-hexadione (35.2 g) in 400 ml acetic acid was refluxed for 48 hours, stripped of solvent, slurried in methylene chloride and filtered. The filtrate was washed with saturated sodium bicarbonate solution, dried and stripped to yield N-(2,5-dimethylpyrrol-1-yl)-phthalimide (98%).

The phthalimide (57.3 g) and hydrazine (8 gm) were refluxed for 4 hours in ethanol and filtered. The filtrate was stripped, redissolved in ether/methylene chloride, filtered and stripped again to yield the title product.

Example 2—Preparation of N-(2,5-dimethyl-pyrrol-1-yl) chloroacetamide

The product of Example 1 (13.2 g) and pyridine (9.48 g) were stripped in ethyl acetate (200 ml) at room temperature with dropwise addition of 13.56 g chloroacetyl chloride. The mixture was stirred overnight, stripped, dissolved in methylene chloride, washed with water, dried and stripped. The residue was chromatographed in a silica gel (325 g) column (chloroform elution), to yield the title product (12.27 g).

Example 3—Preparation of N-(N-methyl-N-propargyl-carbamidomethyl)-N-(2,5-dimethylpyrrol-1-yl) chloroacetamide To the product of Example 2 (3.91 g) in 200 ml DMF was added sodium hydride (1.1 g). After stirring for one hour at 0° C., N-methyl-N-propargyl-bromoacetamide (4 g) was added dropwise. After stirring overnight at room temperature the solution was stripped. The residue was slurried with 150 ml hexane, and chromatographed on silica gel (30 g) with methylene chloride elution. Yield 2.4 g of the title product.

Example 4—Preparatation of ethyl 2-(N-(2,5-dimethyl-pyrrol-yl)-N-chloroacetyl-amino)-propionate The product of Example 2 (3.17 g), ethyl 2-bromopropionate (3.08 g) and sodium hydride (0.86 g) in 200 ml DMF were treated at −15° C. according to the procedure of Example 3. Work-up yielded 1.7 g of the title product (chromatographed on 120 g silica gel column).

Example 5—Preparation of N-(2-methyl-1,3-thiazol-4-yl) methyl-N-(2,5-dimethylpyrrol-1-yl)cloroacetamide The product of Example 2 (5.04 g), 2-methyl-4-chloromethyl-1,3-thiazole (4 g) and sodium hydride (1.56 g) in 120 ml dry DMF were treated at 0° C. according to the procedure of Example 3. Work-up yielded 1.67 g of title product (chromatographed on silica gel and by h.p.l.c.).

Example 6–Preparation of 3-(N-(2,5-dimethylpyrrol-1-yl)-N-chloroacetyl)amino-butan-2-one O-methyloxime The product of Example 2 (6.37 g), 3-bromo-butan-2-one (5.13 g) and sodium hydride (1.52 g) in 150 ml dry DMF were treated according to the procedure of Example 3 to yield 1.5 g 3-(N-(2,5dimethylpyrrol-1yl)-N-chloroacetyl)amino-butan-2one.

The butanone (5 g), methoxylamine hydrochloride (1.8 g) and potassium carbonate (2.9 g) were stirred in 200 methanol at room temperature, stripped, dissolved in methylene chloride, washed, dried and stripped. The residue was purified by h.p.l.c. to yield 1.87 g of title product.

The other compounds of Table I were prepared in the same manner as the above Examples.

TABLE I

COMPOUNDS OF THE FORMULA

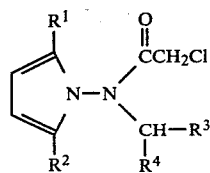

| No. | R¹ | R² | R³ | R⁴ | mp °C. | C Cal | C Fd | H Cal | H Fd | N Cal | N Fd |
|---|---|---|---|---|---|---|---|---|---|---|---|
| 1 | CH₃ | CH₃ | CH₃ | CO₂CH₂CH₃ | oil | 12.39[a] | 11.9[a] | | | | |
| 2 | CH₃ | CH₃ | H | CO₂CH₂CH₃ | 41–43 | 13.03[a] | 14.6[a] | | | | |
| 3 | CH₃ | CH₃ | H | CON(CH₃)₂ | 95 | 13.08[a] | 12.8[a] | | | | |
| 4 | CH₃ | CH₃ | H | CON(CH₃)(CH₂CH=CH₂) | 72–74 | 56.47 | 56.82 | 6.72 | 5.93 | 14.12 | 14.18 |
| 5 | CH₃ | CH₃ | H | CON(CH₃)(CH₂C≡CH) | oil | 56.85 | 56.45 | 6.09 | 5.99 | 14.21 | 14.33 |
| 6 | CH₃ | CH₃ | H | (oxadiazole with CH₃, CH₃) | 44–47 | 50.97 | 48.85 | 5.31 | 5.29 | 19.82 | 1970 |
| 7 | CH₃ | CH₃ | H | (furyl) | 62–63 | 58.54 | 57.55 | 5.63 | 5.62 | 10.51 | 10.19 |
| 8 | CH₃ | CH₃ | H | (isoxazolyl with CH₃) | — | 55.41 | 58.61 | 5.68 | 6.18 | 14.92 | 16.55 |
| 9 | CH₃ | CH₃ | H | (oxazolinyl) | 81–83 | 53.83 | 53.01 | 5.23 | 5.23 | 15.70 | 15.67 |
| 10 | CH₃ | CH₃ | H | (thiazolinyl with CH₃) | 69–71 | 52.44 | 53.48 | 5.38 | 5.75 | 14.12 | 14.53 |
| 11 | CH₃ | CH₃ | H | (thiazolyl) | 88–89 | 50.79 | 51.13 | 4.97 | 5.16 | 14.8 | 14.66 |
| 12 | C₂H₅ | C₂H₅ | H | OCH₃ | 33–38 | 55.71 | 49.46 | 7.35 | 6.56 | 10.83 | 10.06 |
| 13 | CH₃ | CH₃ | H | OCH₃ | 120–127 | 52.06 | 52.18 | 6.51 | 6.50 | 12.15 | 12.46 |
| 14 | CH₃ | CH₃ | CH₃ | C(=NOCH₃)CH₃ | oil | 54.64 | 57.42 | 7.01 | 7.03 | 14.71 | 15.17 |

[a]Chlorine

TABLE II

COMPOUNDS OF THE FORMULA

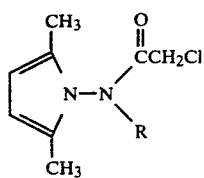

| No. | R | mp °C. | Analysis Cl Cal | Fd |
|---|---|---|---|---|
| A | H | 86–88 | 19.04 | 20.8 |
| B | ![tetrahydrofuranone] | 130–131 | 13.12 | 12.2 |

TABLE A

HERBICIDAL ACTIVITY
% Control Pre/Post

| No. | L | M | P | C | W | O |
|---|---|---|---|---|---|---|
| A | 0/0 | 0/0 | 0/0 | 0/0 | 0/0 | 0/0 |
| B | 0/0 | 0/0 | 35/0 | 0/0 | 0/0 | 0/0 |
| 1 | 20/0 | 10/0 | 25/0 | 93/0 | 100/0 | 95/0 |
| 2 | 0/0 | 0/0 | 0/0 | 85/0 | 98/75 | 90/35 |
| 3 | 40/0 | 20/0 | 50/0 | 92/20 | 98/30 | 95/20 |
| 4 | 0/0 | 10/0 | 0/0 | 70/0 | 99/0 | 90/0 |
| 5 | 0/0 | 0/0 | 35/0 | 90/0 | 100/55 | 85/40 |
| 6 | 0/0 | 15/0 | 25/0 | 70/0 | 100/0 | 93/0 |
| 7 | 70/0 | 55/0 | 70/0 | 95/0 | 100/60 | 100/60 |
| 8 | 0/0 | 0/0 | 60/0 | 90/0 | 100/30 | 60/0 |
| 9 | 90/35 | 35/10 | 98/30 | 95/75 | 100/75 | 93/35 |
| 10 | 20/0 | 20/0 | 20/0 | 100/65 | 100/65 | 95/55 |
| 11 | 0/0 | 0/0 | 50/0 | 100/70 | 100/75 | 95/40 |

TABLE A-continued

HERBICIDAL ACTIVITY
% Control Pre/Post

| No. | L | M | P | C | W | O |
|---|---|---|---|---|---|---|
| 12 | 100/0 | 60/0 | 40/0 | 100/0 | 100/0 | 83/0 |
| 13 | 94/0 | 80/10 | 35/0 | 97/0 | 100/25 | 93/0 |
| 14 | 100/0 | 60/0 | 30/0 | 90/20 | 100/75 | —/55 |

L = Lambsquarter (*Chenopodium album*)
M = Mustard (*Brassica arvensis*)
P = Pigweed (*Amaranthus retroflexus*)
C = Crabgrass (*Digitaria sanguinalis*)
W = Watergrass (*Echinochloa crusgalli*)
O = Wild Oats (*Avena fatua*)

What is claimed is:

1. A compound having the formula:

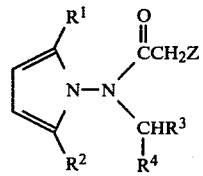

wherein $R^1$ and $R^2$ are alkyl of 1 to 3 carbon atoms or halo; $R^3$ is hydrogen or alkyl of 1 to 3 carbon atoms; z is halo and $R^4$ is isothiazolyl optionally substituted at a ring carbon with an alkyl group having 1 to 4 carbon atoms or phenyl.

2. A compound according to claim 1 wherein $R^1$ and $R^2$ are methyl, z is chloro, and $R^3$ is hydrogen.

3. A compound according to claim 2 wherein $R^4$ is 1,2-thiazol-3yl.

4. A grass herbicidal composition comprising a biologically inert carrier and an herbicidally effective amount of the compound of the formula defined in claim 1.

5. A method for controlling grasses which comprises applying to said vegetation or its growth environment an herbicidally effective amount of the compound of the formula defined in claim 1.

* * * * *